United States Patent [19]

Katsuyama et al.

[11] 4,418,037
[45] Nov. 29, 1983

[54] COLOR INDICATOR COMPOSITION AND FILM FOR DETECTING HYDROGEN PEROXIDE

[75] Inventors: Harumi Katsuyama, Asakashi; Tadao Shishido, Minamiashigarashi, both of Japan

[73] Assignee: Fuji Photo Film Co., Ltd., Kanagawa, Japan

[21] Appl. No.: 369,718

[22] Filed: Apr. 19, 1982

[30] Foreign Application Priority Data

Apr. 17, 1981 [JP] Japan ................................ 56-058068

[51] Int. Cl.$^3$ ...................... G01N 33/52; G01N 33/66
[52] U.S. Cl. ......................................... 422/56; 422/57; 435/14; 435/28; 435/805; 436/95; 436/135; 436/904
[58] Field of Search .................. 422/56, 57; 23/230 B, 23/292; 435/28, 805; 252/408; 436/135, 904

[56] References Cited

U.S. PATENT DOCUMENTS

| | | | |
|---|---|---|---|
| 2,981,606 | 4/1961 | Keston | 23/292 |
| 4,098,574 | 7/1978 | Dappen | 435/28 X |
| 4,119,405 | 10/1978 | Lam | 435/28 X |
| 4,247,631 | 1/1981 | Nix | 435/28 X |
| 4,251,629 | 2/1981 | Yamanisi | 435/28 |
| 4,260,679 | 4/1981 | Tsuda | 435/28 |
| 4,302,537 | 11/1981 | Gundermann | 435/28 X |

*Primary Examiner*—Sidney Marantz
*Attorney, Agent, or Firm*—Sughrue, Mion, Zinn, Macpeak and Seas

[57] ABSTRACT

In a multilayer analysis film for detecting hydrogen peroxide by dry process which comprises a support and a reagent layer having contained therein a color indicator composition comprising peroxidase and a substance capable of causing a optically detectable change in the presence of hydrogen peroxide and peroxidase, the color indicator composition is characterized by further containing specific pyrogallol derivatives. Such pyrogallol derivatives improve stability during storage of such a multilayer analysis film.

17 Claims, 8 Drawing Figures

COLOR INDICATOR COMPOSITION AND FILM FOR DETECTING HYDROGEN PEROXIDE

BACKGROUND OF THE INVENTION

1. Field of the Invention

The present invention relates to a color indicator composition for detecting hydrogen peroxide containing a peroxidase, having improved stability during storage and a quantitative analysis film for detecting hydrogen peroxide comprising the composition which enables operation by a dry process. More particularly, the present invention relates to a color indicator composition for detecting hydrogen peroxide having improved stability during storage which comprises incorporating a specific pyrogallol derivative for preventing inactivation of a peroxidase titer into the composition without substantially interfering with or inhibiting quantitative assay and assaying a detectable chemical species formed by the interaction between a peroxidase and a compound capable of forming a dye through oxidative coupling using hydrogen peroxide as a substrate, as well as a quantitative analysis film for detecting hydrogen peroxide comprising such a composition having improved stability during storage, which enables operation by a dry process.

Various quantitative analysis films, particularly multi-layered analysis films which permit colorimetric analysis of hydrogen peroxide by dry process—in which a peroxidase is involved or which is catalyzed by a peroxidase—have been proposed and some of them have been put in practical use. Among them, there are quantitative analysis films for analysis of glucose, uric acid, cholesterol, choline esterase, creatine, etc., in the living body by a dry process which comprises, in sequence, reacting the same with the appropriate oxidizing enzyme or reacting the reaction product formed during an enzyme reaction with the appropriate oxidiziing enzyme, reacting the thus released hydrogen peroxide with a color indicator to form color, and then measuring the formed color. In order to enhance the speed of examination, avoid complicated operation and reduce cost, demands for dry type quantitative analysis films have increased, particularly in the field of clinical examination. Thus, quantitative analysis films of the test paper sheet type of the single, or dual layer or multi-layered quantitative analysis type with high accuracy in analysis have been developed.

In particular, multi-layer composite type quantitative analysis films are disclosed in Japanese Patent Application (OPI) (the term "OPI" as used herein refers to a "published unexamined Japanese patent application") 53888/74 (corresponding to U.S. Pat. No. 3,992,158) which have markedly improved accuracy in analysis as compared to conventional quantitative analysis films of the test paper sheet type having a single or dual layers. For purposes of further improving accuracy in analysis and in accordance with the analyte to be assayed, hydrogen peroxide indicators having high detection sensitivity have also been provided in such multi-layer composite type quantitative analysis forms; examples of indicators for detecting hydrogen peroxide and layer structures for such multi-layer analysis films are disclosed in Japanese Patent Applications Nos. (OPI) 40191/76 (corresponding to U.S. Pat. No. 4,042,335) 131089/78, 29700/79 (corresponding to U.S. Pat. No. 4,166,093), 124499/80, etc.

Indicators for detecting hydrogen peroxide used for these quantitative analysis films by a dry process are based on those for detecting hydrogen peroxide employed in conventional quantitative analysis by a dry process and the principles are the same.

Particularly, in the field of clinical examination, a variety of components in the living body are converted into common intermediates through chemical reactions having high specificity, generally utilizing an enzyme reaction having particularly high specificity, to thereby effect quantitative determination. As such a common intermediate, hydrogen peroxide has been utilized in many measurement methods. Further, many colorimetric methods which are inexpensive and promise high accuracy have been developed based on combinations of hydroperoxidase—where a substrate is hydrogen peroxide—and related reagents.

Catalase or peroxidase (POD) is often used as hydroperoxidase and, in particular, many combinations with indicators for detecting hydrogen peroxide utilizing peroxidation of peroxidase are known. Indicators for detecting hydrogen peroxide are classified into two groups: (a) reducible chromogens and (b) combination of a hydrogen donor (developing agent) and a coupler. The former was proposed by Keston, A. S., et al. (Keston, A. S., *Specific Colorimetric Enzymatics, Analytical Reagents for Glucose,* Abstracts of Papers, 129th Meeting Am. Chem. Soc. page 31C, April (1956), and the latter by P. Trinder (*Ann. Cli. Biochem.,* 6, 24 (1969) and *J. Clin. Pathol.,* 22, 246 (1969)). Improvements on such reducible chromogens, hydrogen donors or couplers are disclosed in Japanese Patent Publications Nos. 33798/72, 16235/79, 37555/76, 44834/78, 12360/79, 24879/80 and 3394/79, Japanese Patent Applications (OPI) Nos. 86392/77, 26188/78, 50991/74, 11892/75, 40585/78, 110897/80, 25892/79, 20471/80 and 101861/80, Japanese Patent Publication No. 2960/80, etc.

Analytical compositions, test papers and multilayer analysis films utilizing such enzymological methods involve advantages and disadvantages resulting from enzymes which are employed as reagents.

A major reason why a variety of enzyme control complicated phenomena of life perfectly without any error lies in the substrate specificity of an enzyme. By the substrate specificity, an enzyme can lead a desired chemical substance (compound to be tested) selective to its reaction system among a complicated composition. Such a high selectivity is one of extreme advantage that cannot be possessed by ordinary chemical reagents.

On the other hand, however, enzymes also involve disadvantages due to the fact that enzymes are proteins unlike chemical catalysts employed in chemical industries, manufacturing industries, etc., although enzymes catalyze many reactions in vivo under mild conditions. A most serious disadvantage is that inactivation of an enzyme activity is liable to occur due to denaturation of proteins based on thermal denaturation or an irreversible reaction of an active chemical species. That is, an enzyme activity is created by the presence of a delicate active site based on a primary, secondary or high-dimensional structure of a complicated protein; an enzyme is inactivated by occurrence of deformation of a protein in its structure due to a chemical reaction with a reactive chemical species of an external source, physical adsorption or the like. When an enzyme contained in a composition for quantitative assay is inactivated, an expected reaction becomes slow and a function is not effected as originally designed. As a result, an incorrect result on analysis is obtained.

In analytical compositions, test paper, multilayer analysis films, and the like in which enzyme(s) is/are used as a reagent(s), thermal stability is poor; further, properties principally possessed by an enzyme that are liable to be inactivated by a chemically active species determine the efficiency of these analytical compositions so that it is generally difficult to store them over long periods of time. Storability as analytical elements is maintained, on a bare basis, generally by storage under refrigeration, storage under freezing, moisture-proofing storage, etc.

SUMMARY OF THE INVENTION

An object of the present invention is to provide a color indicator composition for detecting hydrogen peroxide using a peroxidase in which storability is improved.

Another object of the present invention is to provide a peroxidase deterioration prevention agent comprising a pyrogallol derivative that does not substantially interfere or inhibit enzymatic reaction.

A further object of the present invention is to provide a color indicator composition for detecting hydrogen peroxide containing a pyrogallol derivative that does not inhibit any color-forming reaction for detecting hydrogen peroxide.

A still further object of the present invention is to provide a quantitative analysis film for detecting hydrogen peroxide containing the foregoing improved color indicator composition for detecting hydrogen peroxide which provides improved stability during storage.

The present invention relates to:

(1) In a color indicator composition for detecting hydrogen peroxide comprising a substance having a peroxidase activity and a substance capable of causing a detectable change in the presence of hydrogen peroxide and the substance having a peroxidase activity, the color indicator composition for detecting hydrogen peroxide comprising a pyrogallol derivative represented by formula (1):

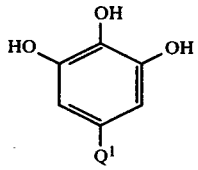

wherein $Q^1$ represents a nitro group, a cyano group, an alkyl group, a substituted alkyl group, an aryl group, a substituted aryl group, an aralkyl group, a carboxyl group or a $-COOQ^2$ group wherein $Q^2$ represents an alkyl group, a substituted alkyl group, an aryl group, a substituted aryl group or an aralkyl group.

(2) A color indicator composition for detecting hydrogen peroxide described in (1) wherein the substance capable of causing a detectable change is a combination of a hydrogen donor and a coupler.

(3) In a quantitative analysis film comprising a reagent layer containing a color indicator composition for detecting hydrogen peroxide comprising a substance having a peroxidase activity and a substance capable of causing a detectable change in the presence of hydrogen peroxide and the substance having a peroxidase activity, the quantitative analysis film wherein the composition contains a pyrogallol derivative represented by formula (1):

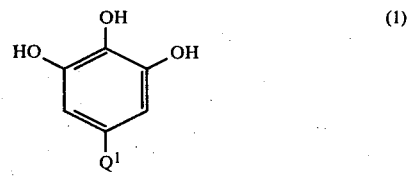

wherein $Q^1$ represents a nitro group, a cyano group, an alkyl group, a substituted alkyl group, an aryl group, a substituted aryl group, an aralkyl group, a carboxyl group or a $-COOQ^2$ group wherein $Q^2$ represents an alkyl group, a substituted alkyl group, an aryl group, a substituted aryl group or an aralkyl group.

(4) A quantitative analysis film as described in (3) wherein the substance capable of causing a detectable change is a combination of a hydrogen donor and a coupler.

(5) A quantitative analysis film as described in (3) or (4) wherein the reagent layer is further composed of a color-forming reaction layer and a dye-fixing layer.

(6) A quantitative analysis film described in (3) or (4) wherein the reagent layer is a single layer.

Preferred embodiments of the present invention are:

(7) The composition described in (2) wherein the hydrogen donor is at least one compound selected from the group consisting of a 4-substituted antipyrine, a 2-hydrazinobenzothiazoline, a p-halogenophenol and an N,N-disubstituted-p-phenylenediamine represented by formula (2):

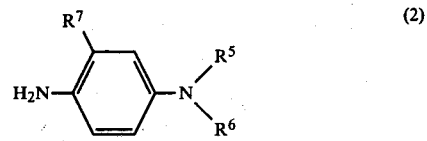

wherein $R^5$ and $R^6$ each represents an alkyl group, an alkoxyalkyl group, a hydroxyalkyl group, a cyanoalkyl group, a halogenoalkyl group or an acylaminoalkyl group and, $R^5$ and $R^6$ may be the same or different; and $R^7$ represents a hydrogen atom, an alkyl group, an alkoxy group or a halogen atom.

(8) The composition described in (2) wherein the coupler is at least one compound selected from the group consisting of a naphthol, a phenol, a pyrazolone and an N,N-disubstituted aniline represented by formula (3):

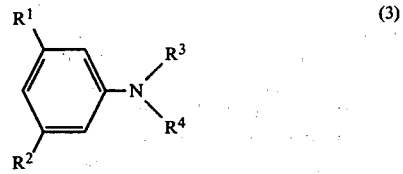

wherein $R^1$ and $R^2$ each represents a hydrogen atom, an alkyl group or an alkoxy group and, $R^1$ and $R^2$ may be the same or different; and $R^3$ and $R^4$ each represents an alkyl group, an alkoxyalkyl group, a hydroxyalkyl group, an aminoalkyl group, a cyanoalkyl group, a halogenoalkyl group or an acylaminoalkyl group and, $R^3$ and $R^4$ may be the same or different.

(9) The composition described in (7) wherein the hydrogen donor is 4-aminoantipyrine.

(10) The quantitative analysis film described in (4), (5) or (6) wherein the hydrogen donor is at least one compound selected from the group consisting of a 4-aminoantipyrine, a 2-hydrazinobenzothiazoline, a p-halogenophenol and an N,N-disubstituted-p-phenylenediamine represented by formula (2):

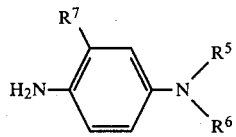

(2)

wherein $R^5$ and $R^6$ each represents an alkyl group, an alkoxyalkyl group, a hydroxyalkyl group, a cyanoalkyl group, a halogenoalkyl group or an acylaminoalkyl group and, $R^5$ and $R^6$ may be the same or different; and $R^7$ represents a hydrogen atom, an alkyl group, an alkoxy group or a halogen atom.

(11) The quantitative analysis film described in (4), (5) or (6) wherein the coupler is at least one compound selected from the group consisting of a naphthol, a phenol, a pyrazolone and an N,N-disubstituted aniline represented by formula (3):

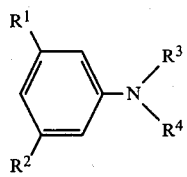

(3)

wherein $R^1$ and $R^2$ each represents a hydrogen atom, an alkyl group or an alkoxy group and, $R^1$ and $R^2$ may be the same or different; and $R^3$ and $R^4$ each represents an alkyl group, an alkoxyalkyl group, a hydroxyalkyl group, an aminoalkyl group, a cyanoalkyl group, a halogenoalkyl group or an acylaminoalkyl group and, $R^3$ and $R^4$ may be the same or different.

(12) The quantitative analysis film described in (4), (5) or (6) wherein the hydrogen donor is 4-aminoantipyrine.

(13) The quantitative analysis film described in (4), (5) or (6) wherein the reagent layer is provided between a support and a porous layer and the porous layer is in a fluid contact with the reagent layer to form an integral form.

(14) The quantitative analysis film described in (4), (5) or (6) wherein the composition is contained in a polymer binder.

(15) The quantitative analysis film described in (4), (5) or (6) wherein the reagent layer further contains a mordanting agent comprising an anionic polymer or a cationic polymer.

(16) The quantitative analysis film described in (5) wherein the dye-fixing layer further contains a polymer mordanting agent comprising an anionic polymer or a cationic polymer.

(17) The quantitative analysis film described in (1) wherein a porous support is impregnated with the composition.

BRIEF DESCRIPTION OF THE DRAWINGS

In FIGS. 1 through 8, numerals indicate:
10: support
20: reagent layer
21: dye-fixing layer 22: color-forming reaction layer
23: reagent-impregnated support 31: porous spreading layer 32: definite area-porous layer 40: light-reflecting layer

DESCRIPTION OF PREFERRED EMBODIMENTS

Figure 1:
FIGS. 1 through 8 are outlined cross-sectional views of representative embodiments of the quantitative analysis film in accordance with the present invention.

In the specification, the term "reagent layer" is used to refer to a layer in which an analyte is converted into a chemically detectable species by means of visible light, near ultraviolet light or a near infrared light and which basically comprises a substance having peroxidase activity and a compound capable of causing a detectable change in the presence of hydrogen peroxide and the substance having peroxidase activity.

The term "color-forming reaction layer" refers to a layer in which an analyte is converted into a chemically detectable species.

The term "dye-fixing layer" refers to a layer which contributes to an improvement in detection efficiency of the chemically detectable species.

The reagent layer can be a color-forming reaction and dye-fixing layer when the reagent layer is a single layer and the reagent layer can also be divided into at least two layers, one of which is a color-forming reaction layer and another is a dye-fixing layer. In other words, a color-forming reaction layer and a dye-fixing layer can also be collectively referred to as a reagent layer.

The chemically detectable species is directly or indirectly indicative of the presence and/or concentration of a desired analyte, or a reaction or decomposition product of the analyte.

The term "substance having peroxidase activity" is used to mean a substance which catalyzes oxidation of a hydrogen donor with hydrogen peroxide (as a substrate) and is well recognized in the art (I. Yamazaki et al., *MOLECULAR & CELLULAR BIOCHEMISTRY*, vol. 2(1), pp. 39–52 (1973)). The substance having peroxidase activity takes part in the oxidation of a hydrogen donor with hydrogen peroxide in accordance with the following reaction scheme:

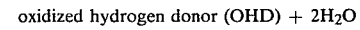

oxidized hydrogen donor (OHD) + 2H$_2$O

The term "hydrogen donor" refers to a compound which is an oxygen acceptor which, in its oxidized state, couples with a coupler such as a naphthol, a phenol, a pyrazolone or the N,N-disubstituted anilines of formula (3). Of these hydrogen donors, the pyrazolones and N,N-disubstituted anilines of formula (3) are particularly preferred.

The color indicator composition for detecting hydrogen peroxide (hereafter sometimes merely referred to as "color indicator for detecting hydrogen peroxide") is a composition capable of producing a compound (hereafter referred to as a "dye") that is detectable by visible light, near ultraviolet light or near infrared light, produced as a result of chemical interaction in the presence of hydrogen peroxide. Further, the indicator for detecting hydrogen peroxide of the present invention can not only detect a color of or quantitatively determine hydrogen peroxide but also detect and quantitatively determine its precursor by the use of a reagent composition capable of producing hydrogen peroxide as a result of chemical interaction with a compound capable of producing hydrogen peroxide, if necessary (hereafter referred to as a "precursor") in combination.

Examples of substances having peroxidase activity include peroxidase extracted from various organisms, synthetic peroxidase and other chemical substances extracted from organisms which exhibit an activity similar to peroxidase, as disclosed in Japanese Patent Application (OPI) No. 137192/75. Of these, peroxidase is preferred.

As the indicator composition for detecting hydrogen peroxide comprising a substance having a peroxidase activity and a compound capable of causing a detectable change in the presence of hydrogen peroxide and the substance having peroxidase activity, chromogens which give a colored compound detectable by its own oxidation, such as benzidine or phenylene diamine known from the old, 3,3',5,5'-tetramethylbenzidine as disclosed in Japanese Patent Application OPI No. 89491/76 triarylimidazoles as disclosed in Japanese Patent Application OPI No. 26188/78 (corresponding to U.S. Pat. No. 4,019,747), etc.; a combination of a hydrogen donor and a coupler which gives a detectable colored compound by oxidative coupling reaction therebetween, and the like can be employed in the present invention.

As hydrogen donors which are contained in the color indicator, 4-substituted antipyrines (4-substituted-2,3-dimethyl-1-phenyl-3-pyrazolin-5-ones) as disclosed in Japanese Patent Application (OPI) No. 50991/74 (corresponding to U.S. Pat. No. 3,983,005) and other known 4-substituted antipyrines; N,N-disubstituted-o- or p-phenylenediamines as disclosed in Japanese Patent Application (OPI) No. 137192/75 (corresponding to U.S. Pat. No. 3,886,045) and other known N,N-disubstituted-o- or p-phenylenediamines; 2-hydrazonobenzothiazolines as disclosed in Japanese Patent Application (OPI) No. 20471/80 and other known 2-hydrazonobenzothiazolines; p-halogenophenols as disclosed in Japanese Patent Application (OPI) No. 148100/80 and other p-halogenophenols and N,N-disubstituted phenylenediamines as represented by formula (2) above can be employed.

Specific examples of useful 4-substituted antipyrines include 4-aminoantipyrine (CAS Registry Number (83-07-8); hereafter the same), 4-(dimethylamino)antipyrine (pyramidon (58-15-1)), 4-(ethylaminoantipyrine) (15166-10-6), 4-(methylamino)antipyrine (noramidopyrine, (519-98-2)), 4-(sodium sulfonatomethylamino)antipyrine (sulphamipyrine (129-89-5)), 4-(sodiumsulfonatomethyl)(isobutyl)aminoantipyrine (dibupyrone (1046-17-9)), 4-(sodium sulfonatomethyl)(methyl)amino antipyrine (methampyrone, (5907-38-0)) and 4-isopropylantipyrine (propiphenazone, (479-92-5)). As other compounds having a similar structure, there are 4-amino-2,3-dimethyl-1-p-tolyl-3-pyrazolin-5-one (56430-10-5) and 4-amino-1,3-diphenyl-2-methyl-3-pyrazolin-5one (52744-73-7). Also, 2-(dimethylamino)-5-phenyl-2-oxazolin-4-one (tozalinone, (1046-17-9)) can be employed.

In the case where substituents $R^5$ and $R^6$ in N,N-disubstituted-p-phenylenediamines represented by formula (2) are alkyl groups, the alkyl group can be a straight or branched lower alkyl group having 1 to 5 carbon atoms; specific examples thereof include a methyl group, an ethyl group, a propyl group, a butyl group, a pentyl group, an isopropyl group, an isobutyl group, an isoamyl group, a t-butyl group and a neopentyl group. In the case of an alkoxyalkyl group, the alkoxyalkyl group comprises a lower alkyl group having 1 to 3 carbon atoms on which a lower alkoxy group having 1 to 3 carbon atoms is substituted; specific examples include a methoxymethyl group, a 2-methoxyethyl group, a 1-methoxyethyl group, a 3-methoxypropyl group, a 2-methoxypropyl group, an ethoxypropyl group and a 2-ethoxyethyl group. In the case of a hydroxyalkyl group, the hydroxyalkyl group comprises a straight or branched lower alkyl group having 1 to 5 carbon atoms on which a hydroxyl group is substituted; specific examples include a hydroxymethyl group, a 2-hydroxyethyl group, a 1-hydroxyethyl group, a 3-hydroxypropyl group, a 2-hydroxypropyl group, a 4-hydroxybutyl group and a 5-hydroxypropyl group. In the case of a cyanoalkyl group, the cyanoalkyl group comprises a straight or branched lower alkyl group having 1 to 5 carbon atoms on which a cyano group is substituted; specific examples thereof include a cyanomethyl group, a 2-cyanoethyl group, a 1-cyanoethyl group, a 3-cyanopropyl group, a 2-cyanopropyl group and a 5-cyanopentyl group. In the case of a halogenoalkyl group, the halogenoalkyl group comprises a straight or branched lower alkyl group having 1 to 5 carbon atoms on which a fluorine, chlorine, bromine or iodine atom is substituted as a halogen atom; specific examples thereof include a fluoromethyl group, a chloromethyl group, a bromomethyl group, a 2-fluoroethyl group, a 1-chloroethyl group, a 2-chloroethyl group, a 2-bromoethyl group and a 3-chloropropyl group. In the case of an acylaminoalkyl group, the acylaminoalkyl group comprises a straight or branched lower alkyl group having 1 to 5 carbon atoms on which an acetamido group, a propionamido group, a benzamido group, a toluamido group, a methanesulfonamido group, a benzenesulfonamido group or a toluenesulfonamido group is substituted as an acylamino group (1 to 10 carbon atoms); specific examples include an acetamidomethyl group, a propionamidomethyl group, a benzamidomethyl group, a p-toluamidomethyl group, a methanesulfonamidomethyl group, an ethanesulfonamidomethyl group, a benzenesulfonamidomethyl group, a p-toluenesulfonamidomethyl group, a 2-acetamidoethyl group, a 2-propionamidoethyl group, a 2-benzamidoethyl group, a 2-p-toluamidoethyl group, a 2-methanesulfonamidoethyl group, a 2-(ethanesulfonamido)ethyl group, a 2-(benzenesulfonamido)ethyl group, a 2-(p- toluenesulfonamido)ethyl group, a 3-acetamidopropyl group and a 3-benzamidopropyl group.

In the case substituents $R^1$ and $R^2$ in the N,N-disubstituted aniline represented by formula (1) represent an alkyl group or an alkoxy group, specific examples thereof are the same as the specific examples in the case that substituent $R^5$ or $R^6$ in the N,N-disubstituted-p-phenylenediamine represented by formula (2) described above represent an alkyl group or an alkoxy group.

In the case $R^3$ and $R^4$ represent an alkyl group, an alkoxyalkyl group, a hydroxyalkyl group, a cyanoalkyl group, a halogenoalkyl group or an acylaminoalkyl group, specific examples thereof are the same as the specific examples in the case where $R^5$ or $R^6$ represent an alkyl group, an alkoxyalkyl group, a hydroxyalkyl group, a cyanoalkyl group, a halogenoalkyl group or an acylaminoalkyl group. In the case $R^3$ and $R^4$ represent an aminoalkyl group, the aminoalkyl group comprises a straight or branched lower alkyl group having 1 to 5 carbon atoms on which an amino group is substituted; specific examples include an aminomethyl group, a 2-aminoethyl group, a 1-aminoethyl group, a 3-aminopropyl group and a 2-aminopropyl group.

Preferred substitutents as $R^1$ and $R^2$ are a hydrogen atom, an alkyl group (1 to 5 carbon atoms) and an alkoxy group (1 to 3 carbon atoms); specific examples of the alkyl group are a methyl group, an ethyl group, a propyl group and, as the alkoxy group, there are a methoxy group and an ethoxy group.

Preferred substituents as $R^3$ or $R^4$ are an alkyl group, an alkoxyalkyl group, a hydroxyalkyl group, a cyanoalkyl group and a halogenoalkyl group; specific examples include a methyl group, an ethyl group, a propyl group; a methoxymethyl group, a 2-methoxyethyl group, a 3-methoxypropyl group, an ethoxymethyl group, a 2-ethoxyethyl group; a hydroxymethyl group, a 1-hydroxyethyl group, a 2-hydroxyethyl group, a 2-hydroxypropyl group, a 3-hydroxypropyl group; a cyanomethyl group, a 2-cyanoethyl group; a chloromethyl group, a 1-chloroethyl group, a 2-chloroethyl group, a 2-chloropropyl group, a 3-chloropropyl group, a bromomethyl group, a 2-bromomethyl group, a fluoromethyl group and a 2-fluoroethyl group.

Specific examples of N,N-disubstituted anilines represented by formula (3) include the following compounds:
N,N-Dimethylaniline
N,N-Diethylaniline
N-Methyl-N-hydroxymethylaniline
N-Methyl-N-(2-hydroxyethyl)aniline
N-Ethyl-N-(2-hydroxyethyl)aniline
N-Methyl-N-(2-methoxyethyl)aniline
N-Ethyl-N-(2-methoxyethyl)aniline
N-Ethyl-N-(2-ethoxyethyl)aniline
N,N-Dimethyl-m-toluidine
N,N-Diethyl-m-toluidine
N,N-Bis(hydroxymethyl)-m-toluidine
N,N-Bis(2-hydroxyethyl)-m-toluidine
N,N-Bis(2-hydroxypropyl)-m-toluidine
N,N-Bis(3-hydroxypropyl)-m-toluidine
N-Methyl-N-hydroxymethyl-m-toluidine
N-Ethyl-N-2-hydroxyethyl-m-toluidine
N-Ethyl-N-hydroxymethyl-m-toluidine
N-Methyl-N-methoxymethyl-m-toluidine
N-Ethyl-N-methoxymethyl-m-toluidine
N-Ethyl-N-2-methoxyethyl-m-toluidine
N-Cyanomethyl-N-hydroxymethyl-m-toluidine
N-Methyl-N-2-chloroethyl-m-toluidine
N-Ethyl-N-2-chloroethyl-m-toluidine
N-2-Cyanoethyl-N-2-hydroxyethyl-m-toluidine
N,N-Dimethyl-m-anisidine
N,N-Diethyl-m-anisidine Of these compounds, preferred N,N-disubstituted anilines are the following:
N,N-Bis(2-hydroxyethyl)-m-toluidine
N-Ethyl-N-2-hydroxyethyl-m-toluidine
N-2-Cyanoethyl-N-2-hydroxyethyl-m-toluidine
N,N-Dimethyl-m-anisidine
N,N-Diethyl-m-anisidine Phenols, naphthols and 5-pyrazolone type couplers which are employed as couplers in the present invention are well known in the photographic art and are described in, e.g., T. H. James, *The Theory of the Photographic Process*, 4th Edition, Chapter 12, pages 335 to 372, subtitled "Principles and Chemistry of Color Photography", published Macmillan Publishing Co., Inc., New York (1977), etc.

Specific examples of these couplers are given below:

Phenol and Naphthol Type Couplers phenol, 2,4-dichlorophenol, 2,6-dichlorophenol, p-hydroxybenzoic acid, m-hydroxybenzoic acid, o-bromophenol, 4,6-dichloro-o-cresol, 2,4-dibromophenol, N-octyl-4-methoxysalicylamide, 4-acetamino-N-hydroxyethylsalicylamide, α-naphthol, β-naphthol, 1,7-dihydroxynaphthalene, N,N-dimethyl-1-hydroxy-2-naphthamide, N-propyl-1-hydroxy-2-naphthamide, 1-naphthol-2-sulfonic acid, 1,8-dihydroxynaphthalene-3,6-disulfonic acid, 1-naphthol-3-sulfonic acid, 1-naphthol-8-sulfonic acid, 2,3-dihydroxynaphthalene-6-sulfonic acid, p-hydoxydiphenyl-1,5-dihydroxynaphthalene, 3,5-dihydroxy-2-naphthoenic acid, etc.

5-Pyrazolone Type Couplers 3-methyl-1-phenyl-5-pyrazolone, 3-methyl-1-(p-sulfophenyl)-5-pyrazolone, 1,3-diphenyl-5-pyrazolone, 3-acetamino-1-(2',4',6'-trichlorophenyl)-5-pyrazolone, 3-anilino-1-(p-sulfophenyl)-5-pyrazolone.

While the mechanism of the present invention is not clearly understood yet, it is assumed as follows:

It is known that an oxidation product of a certain compound, particularly a mono electron-oxidation product of a nitrogen-containing compound or the like, inactivates peroxidase; in particular, an oxidation product of a hydrogen donor has a marked activity of inactivating peroxidase. Thus, a variety of antioxidants were added to a hydrogen donor, attempting to prevent oxidation of the hydrogen donor and it has been found that 1,2-dihydroxynaphthalene and naphthol derivatives have a tendency not to inactivate peroxidase and at the same time also to prevent oxidation of the hydrogen donor, and pyrogallol derivatives exhibit a marked effect among them.

Of pyrogallol derivatives, pyrogallol compounds that do not oxidatively couple with hydrogen donors, i.e., pyrogallol compounds bearing a non-releasable substituent at the 5-position thereof, exhibit an extremely marked effect of stabilizing peroxidase.

It is assumed that the effect of stabilizing peroxidase achieved by pyrogallol derivatives contained in the peroxidase-containing color indicator composition for detecting hydrogen peroxide would be due to prevention from forming the oxidation product—which inactivates peroxidase—produced as a result of the interaction among oxygen and moisture in the air, and peroxidase, a hydrogen donor, the remaining moisture and the like contained in the composition, during storage of the composition. Details of the mechanism why such a specific function for preventing oxidation is exhibited by pyrogallol derivatives are unknown, but it is assumed that there would be a specificity that the oxidation product of the pyrogallol derivatives would not inactivate peroxidase.

The pyrogallol derivatives which can be employed in accordance with the present invention do not interfere with colorimetric determination and are represented by formula (1) above. In case where substituent $Q^1$ is an alkyl group, the alkyl group contains 1 to 20 carbon atoms and can be straight or branched chain; specific examples thereof are a methyl group, an ethyl group, a propyl group, a butyl group, a pentyl group, a hexyl group, an octyl group, a nonyl group, a decyl group, a dodecyl group, an octadecyl group, an eicosyl group, an isopropyl group, an isobutyl group, an isoamyl group, a 4-methylpentyl group, a 6-methylheptyl group, etc.

In the case where substituent $Q^1$ represents a substituted alkyl group, the substituted alkyl group contains 1 to 5 carbon atoms and can be straight or branched chain on which at least one of a hydroxyl group, a cyano group and/or a halogen atom (a fluorine, chlorine, bromine or iodine atom) is borne as a substituent(s). Specific examples of the substituted alkyl group include a hydroxymethyl group, a 2-hydroxyethyl group, a 1-hydroxyethyl group, a 3-hydroxypropyl group, a 2-hydroxypropyl group, a 4-hydroxybutyl group, a 5-hydroxypentyl group, a cyanomethyl group, a 2-cyanoethyl group, a 1-cyanoethyl group, a 3-cyanopropyl group, a 5-cyanopentyl group, a fluoromethyl group, a chloromethyl group, a bromomethyl group, a 2-fluoroethyl group, a 1-chloroethyl group, a 2-chloroethyl group, a 2-bromoethyl group, a 3-chloropropyl group, etc.

The aryl group represented by substituent $Q^1$ preferably contains 6 to 14 carbon atoms. Preferred examples of such aryl groups include a phenyl group, a 1-naphthyl group, a 2-naphthyl group, a 2-indenyl group, a 4-biphenyl group, etc.

The substituted aryl group represented by substituent $Q^1$ preferably contains 6 to 14 carbon atoms as the aryl moiety. Preferred examples of such substituted aryl groups include the foregoing aryl groups on which a substituent such as a halogen atom (a fluorine, chlorine, bromine or iodine atom), a cyano group, a nitro group or a straight or branched lower alkyl group having 1 to 5 carbon atoms is present. Specific examples of such substituted aryl groups include a p-fluorophenyl group, a p-chlorophenyl group, a m-bromophenyl group, a p-cyanophenyl group, a m-nitrophenyl group, a p-tolyl group, a m-tolyl group, a p-ethylphenyl group, a m-cumenyl group, a mesityl group, a 4-chloro-1-naphthyl group, a 5-methylnaphthyl group, etc.

The aralkyl group represented by substituent $Q^1$ preferably contains 7 to 20 carbon atoms and specific examples of such aralkyl groups include a benzyl group, a phenethyl group, a 1-naphthylmethyl group, a 2-naphthylmethyl group, etc.

In the case where substituent $Q^1$ is represented by the —COO$Q^2$ group and $Q^2$ represents an alkyl group, a substituted alkyl group, an aryl group, a substituted aryl group or an aralkyl group, preferred examples of such —COO$Q^2$ groups are the same as the case where substituent $Q^1$ is an alkyl group, a substituted alkyl, an aryl group, a substituted aryl group or an aralkyl group, respectively.

Preferred examples of substituent —COO$Q^2$ are a carboxyl group, a methoxycarbonyl group, an ethoxycarbonyl group, a propoxycarbonyl group, a butoxycarbonyl group, a pentyloxycarbonyl group, an octyloxycarbonyl group, a decyloxycarbonyl group, an octadecyloxycarbonyl group, an isopropoxycarbonyl group, an isobutoxycarbonyl group, an isoamyloxycarbonyl group, a 2-chloroethoxycarbonyl group, a 3-chloropropoxycarbonyl group, a phenoxycarbonyl group, a p-tolyloxycarbonyl group, a benzyloxycarbonyl group, a phenethyloxycarbonyl group, a cyano group, a nitro group, a methyl group, an ethyl group, a propyl group, a butyl group, a pentyl group, an isopropyl group, an isobutyl group and an isoamyl group.

Preferred examples of pyrogallol derivatives include gallic acid, methyl gallate, ethyl gallate, propyl gallate, isopropyl gallate, pentyl gallate, isoamyl gallate, octyl gallate, stearyl gallate, β-chloroethyl gallate, phenyl gallate, p-tolyl gallate, benzyl gallate, phenethyl gallate, 5-cyanopyrogallol, 5-nitropyrogallol, 5-methylpyrogallol, 5-ethylpyrogallol, 5-propylpyrogallol, 5-butylpyrogallol, 5-pentylpyrogallol, 5-isopropylpyrogallol, 5-isobutylpyrogallol, 5-isoamylpyrogallol, etc.

The color indicator composition for detecting hydrogen peroxide or the quantitative analysis film in accordance with the present invention can further contain a mordanting agent. As such mordanting agents, cationic polymers as described in Japanese Patent Applications OPI Nos. 40191/76 (corresponding to U.S. Pat. No. 4,042,335), 89796/78 (corresponding to U.S. Pat. No. 4,069,017), 131089/78 (corresponding to U.S. Pat. No. 4,144,306) and *The Theory of the Photographic Process,* supra, pages 366 to 372, as well as anionic polymers as will be later described, can be employed. In the case that the color indicator for detecting hydrogen peroxide used in the present invention forms a dye capable of forming an anion as a result of the chemical ineraction in the presence of hydrogen peroxide, cationic compounds such as cationic polymers are employed; and in the case that cationic dyes are formed, needless to say, anionic compounds such as anionic polymers are employed. It is further needless to say one should employ mordanting agents that do not absorb, i.e., that do not interfere colorimetric analysis. Hereafter, the present invention will be described in more detail with reference to cases where a cationic polymer mordanting agent or an anionic polymer mordanting agent is used as a mordanting agent, wherein the term "mordanting polymer" is used herein to collectively mean both cationic and anionic polymers.

The anionic polymer employed in the present invention is a polymer containing the anionic group defined above in the polymer backbone itself or in the organic group (Org in Formula (AP) below) bound to the polymer backbone. In addition to conventional anionic polymers, acid type cation ion exchange resins can also be employed as the anionic polymer; preferably the conventional anionic polymers or cation ion exchange resin are water-soluble polymers or polymers which are capable of being swollen by water (water-swellable). The anionic polymers can be employed singly or as a combination of two or more. Anionic polymers with and without film forming capability can both be employed but it is preferred that anionic polymers having no film-forming capability be employed in combination with binder polymers having film forming capability.

Specific examples of anionic polymers include polymers or copolymers having a structure where a carboxylate group (—COO$^\ominus$), a sulfonate group (—SO$_3^\ominus$) or a phosphonate group (—PO$_3^{2\ominus}$) is bound as an anionic atomic group, or the aforesaid anionic atomic group containing a counter cation is bound, to all of the constitutional repeating units (hereafter referred to as "CRU") of the high molecular chain thereof or to a part of the CRU (the arrangement may be either orderly or at random). As counter cations, there are alkali metal ions (e.g., Li$^\oplus$, Na$^\oplus$, K$^\oplus$, Cs$^\oplus$), alkaline earth metal ions (e.g., Mg$^{2\oplus}$, Ca$^{2\oplus}$, Sr$^{2\oplus}$, Ba$^{2\oplus}$) and ammonium ions (NH$_4^\oplus$).

These anionic polymers are shown by formula (AP):

$$\text{Org} \rightarrow \text{CB} - Z^\ominus A^\oplus \quad \text{(AP)}$$

wherein Org represents an organic group and constitutes a portion of a polymer backbone, CB represents a chemical bond(s) or a chemical group linking $Z^{\ominus}$ to Org, $Z^{\ominus}$ represents a carboxylate group; ($-COOR^{\ominus}$), a sulfonate group ($-SO_3^{\ominus}$) or a phosphonate group ($-PO_3^{2\ominus}$) and $A^{\oplus}$ is a counter cation as mentioned above.

Specific examples of anionic polymers containing the aforesaid CRU include the following:

Alkali hydrolysates of a metal vinyl ether-maleic anhydride copolymer (copolymer containing dilithium, disodium or dipotassium 1,2-dicarboxylate ethylene as the CRU);

Alkali metal salt or alkaline earth metal salt of a polyacrylic acid;

Alkali metal salt or alkaline earth metal salt of a poly-N-($\beta$-sulfo-$\alpha,\alpha$-dimethylethyl)acrylamide;

Alkali metal salt or alkaline earth metal salt of a polystyrene-p-sulfonic acid;

Alkali metal salt or alkaline earth metal salt of a copolymer of styrene-p-sulfonic acid and a hydrophilic vinyl monomer (examples of hydrophilic vinyl monomers: acrylic acid, acrylic acid alkyl esters (e.g., methyl acrylate), acrylic acid hydroxyalkyl esters (e.g., $\beta$-hydroxyethyl acrylate), acrylamides (e.g., acrylamide, N-methylacrylamide, N-isopropylacrylamide, N-($\beta$-sulfonato-$\alpha,\alpha$-dimethylethyl)acrylamide, N-ethyl-N-isopropylacrylamide, acrylmorpholide

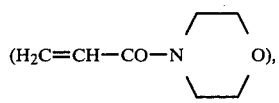

N-acryloylpiperidine, N-acryloylpiperidine, N-acryloylpiperazine), methacrylic acid hydroxyalkyl esters (e.g., $\beta$-hydroxyethyl methacrylate), methacrylamides (e.g., methacrylamide, methacryl morpholide));

Alkali metal salts of a polyvinylphosphonic acid:

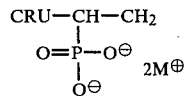

where M is lithium, sodium or potassium); Carboxymethyl cellulose; Carboxyethyl cellulose; Alginic acid and alkali metal salts thereof;

Typical examples of preferred anionic polymers include the following:
Polystyrene-p-potassium sulfonate
Styrene-p-potassium sulfonate-acrylmorpholide copolymer
Styrene-p-potassium sulfonate-acrylamide copolymer
Styrene-p-potassium sulfonate-N-isopropylacrylamide copolymer
Styrene-p-sodium sulfonate-N-ethyl-N-isopropylacrylamide copolymer
Poly-N-($\beta$-potassium sulfonato-$\alpha,\alpha$-dimethyl)acrylamide
N-($\beta$-potassium sulfonato-$\alpha,\alpha$-dimethylethyl)acrylamide-$\beta$-hydroxyethyl acrylate copolymer
N-($\beta$-potassium sulfonato-$\alpha,\alpha$-dimethylethyl)acrylamide-N-ethylacrylamide copolymer Of these anionic polymers, polystyrene type anionic polymers (in formula (AP), CB is a phenylene group) are most preferred.

The anionic polymer can be incorporated into a layer containing the color indicator for detecting hydrogen peroxide or a dye-fixing layer containing the anionic polymer—but containing no other reagent component—can also be provided as a layer separately from a layer containing the color indicator for detecting hydrogen peroxide. Further, the anionic polymer can also be incorporated both into a layer containing the color indicator for detecting hydrogen peroxide and into the dye-fixing layer. The anionic polymer can also be employed as a combination of two or more thereof if desired or necessary, although only one is generally sufficient.

In the case that the anionic polymer is incorporated both into a layer containing the color indicator for detecting hydrogen peroxide and into the dye-fixing layer, both anionic polymers can be the same or they can differ. Further, if desired or necessary, the anionic polymer can also be incorporated into a layer other than a layer containing the color indicator for detecting hydrogen peroxide or a dye-fixing layer.

Any or all of the reagent layer containing the color indicator for detecting hydrogen peroxide and the mordanting polymer, a color reaction layer containing the color indicator for detecting hydrogen peroxide and the dye-fixing layer containing the mordanting polymer of the quantitative analysis film in accordance with the present invention can contain a binder polymer. As binder polymers, known hydrophilic polymers such as gelatin, casein, agarose, starch, polyvinyl alcohol, polyvinyl pyrrolidone, polyacrylamide, polyethylene glycol, etc., can be employed and, in combination with these hydrophilic polymers, known hardeners (hardening agents or cross linking agents) can also be employed.

The reagent layer, the color-forming reaction layer or the dye-fixing layer is formed either by dispersing or dissolving a mixture of the color indicator for detecting hydrogen peroxide and the mordanting polymer or the color indicator for detecting hydrogen peroxide and the mordanting polymer, respectively, in a binder polymer and then coating the dispersion or solution onto a support by a conventional coating technique followed by drying or by impregnating the surface of or the interior of a porous support with the dispersion or solution. In the case where the reagent layer, the color reaction layer or the dye-fixing layer is provided on a support by coating, the layer thickness of each is in a range of from 1 $\mu$m to 100 $\mu$m, preferably 2 $\mu$m to 50 $\mu$m. In the case that the dye-fixing layer is composed only of the mordanting polymer free of any binder polymer, the layer thickness is in the range of from 1 $\mu$m to 50 $\mu$m, preferably 3 $\mu$m to 30 $\mu$m.

Hereafter, the present invention will be described with reference to the drawings showing embodiments of the present invention.

FIG. 1 is a quantitative analysis film comprising reagent-impregnated support 23 obtained by impregnating a self-supporting porous support with a reagent composition containing the color indicator for detecting hydrogen peroxide on the surface thereof and in the interior thereof.

As self-supporting porous supports, known film-like or sheet-like supports such as a filter paper, conventional paper, non-woven cloth, membrane filter, a porous plastic film, etc., can be employed. In the case that the quantitative analysis film is to be installed in a slide frame as disclosed in Japanese Patent Applications (OPI) Nos. 156079/79 and 160296/79 (which corresponds to OPI No. 63452/82), Japanese Utility Model Application 41787/80 (which correspond to OPI No. 142,454/81.). Japanese Patent Application 138100/80, etc., flexible materials such as fabrics can also be employed in addition to the materials described above as the porous support. Such a quantitative analysis film can be employed by adhering it onto a film-like or sheet-like support using a hot melt adhesive or an adhesive tape and the layer structure in this case is similar to that of a quantitative analysis film shown in FIG. 2, which will subsequently be described.

Figure 2:
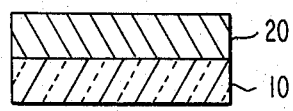

FIG. 2 shows a quantitative analysis film having such a structure that reagent layer 20 containing the color indicator for detecting hydrogen peroxide and the mordanting polymer is provided on film-like or sheet-like support 10. The support 10 can be either transparent or opaque.

Figure 3:
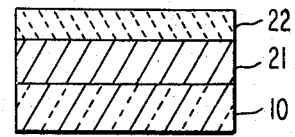

FIG. 3 shows a quantitative analysis film having such a structure that dye-fixing layer 21 containing the mordanting polymer and color-forming reaction layer 22 containing the color indicator for detecting hydrogen peroxide are provided, in this sequence, on a film-like or sheet-like support. The support can be either transparent or opaque but it is preferably a transparent support.

In quantitative analysis films as shown in FIG. 4 through FIG. 8, a reagent layer, a color-forming reaction layer or a dye-fixing layer is provided between a support and a porous layer and the porous layer is brought into fluid contact (this definition is disclosed in Japanese Patent Application (OPI) No. 40191/76, EPC Application No. 0013156, etc., described above i.e., a mode of contact having the ability of a fluid, whether liquid or gaseous, to pass between layers) with the reagent layer, the color-forming layer or the dye-fixing layer; preferably, the analysis film has such a structure that these layers are adhered in a unitary or integral form.

The porous layer is employed as a porous spreading layer or a definite area-porous layer which have the function that when a sample liquid is spotted thereon the sample liquid is supplied onto a layer therebeneath and preferably has the function of rendering the quantity of the liquid sample per unit area approximately constant (in the case of the porous spreading layer), or which has the function of spreading into the same area of its shape to thereby render the quantity of the liquid sample per unit are approximately constant (in the case of the definite area-porous layer), in both cases the liquid sample being supplied to a layer therebeneath. In more detail, the latter porous layer has a definite area so that an amount of a liquid sample held in the porous layer is determined by the definite area and the thus determined amount of the liquid sample is transferred to a layer therebeneath (ordinarily a reagent layer) in the same amount and area as in the porous layer, since a possible expansion of the porous layer due to holding the liquid sample is negligible in the width direction when compared to the thickness direction.

It is sufficient that the porous layer has voids to provide transport of the liquid sample but in general, it is preferred that the void volume of the porous layer be in the range of from about 30 to about 85%. Void volume can be calculated by the technique described in Chalkley, *Journal of the National Cancer Institute*, vol. 4, page 47 (1943) and by direct weighing and determining the ratio of actual weight of the structure to the weight of solid material equal in volume to that of the structure.

Figure 4:
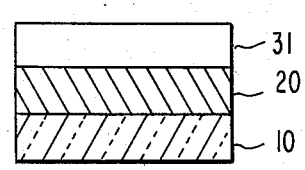

FIG. 4 shows a quantitative analysis film having a structure comprising film-like or sheet-like support 10 having provided thereon reagent layer 20 containing the color indicator for detecting hydrogen peroxide and the mordanting polymer and porous spreading layer 31, in this sequence.

Figure 5:
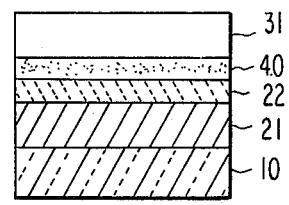

FIG. 5 shows a quantitative analysis film comprising film-like or sheet-like support 10 having provided thereon dye-fixing layer 21 containing the mordanting polymer, color-forming reaction layer 22 containing the color indicator for detecting hydrogen peroxide, light-reflecting layer 40 and porous spreading layer 31, in this sequence.

As the porous spreading layer of the quantitative analysis film shown in FIG. 4 or FIG. 5, a porous layer having dispersed therein finely divided porous powders such as blush polymers (generally called membrane filters) as disclosed in Japanese Patent Application (OPI) No. 53888/74 (corresponding to U.S. Pat. No. 3,992,158), diatomaceous earth, microcrystalline materials (e.g., microcrystalline cellulose (Avicel, tradename of FMC Corporation)) in a binder polymer, porous aggregates formed by allowing fine spherical beads of glass or polymers to adhere to one another in point-to-point contact; a non-fibrous isotropic porous layer such as an aggregated three-dimensional lattice particle structure formed by allowing fine spherical beads of water-nonswellable organic polymers to adhere to one another using a water-insoluble adhesive in point-to-point contact, etc., as disclosed in Japanese Patent Application (OPI) No. 90589/80 (corresponding to U.S. Pat. No. 4,258,001); a fibrous anisotropic layer comprising fabrics rendered hydrophilic as disclosed in Japanese Patent Application (OPI) No. 164356/80 (corresponding to U.S. Pat. No. 4,292,272), fabrics which are rendered physically hydrophilic (e.g., by a glow discharge, a plasma treatment, corona discharge, ultraviolet irradiation, a flame treatment etc.) as disclosed in Japanese Patent Application (OPI) No. 140532/80, filter paper, etc.; can be employed.

The method for providing a non-fibrous isotropic porous layer onto reagent layer 20 or light-reflecting layer 40 as a porous spreading layer can be in accordance with the techniques disclosed in Japanese Patent Applications (OPI) Nos. 53888/74 (corresponding to U.S. Pat. No. 3,992,158), 90589/80 (corresponding to U.S. Pat. No. 4,258,001), etc., described above or a method for providing the fibrous anisotropic porous spreading layer onto reagent layer 20 or light-reflecting layer 40 as a porous spreading layer can be in accordance with the techniques disclosed in Japanese Patent Application (OPI) No. 164356/80 and Japanese Patent Application No. 140532/80 (corresponding to OPI No. 66359/82) described above.

The definite area-porous layer can be provided using materials (e.g., fabrics, paper, membrane filters) and in accordance with the method disclosed for the porous layer in Japanese Utility Model Application No. 120299/80 (corresponding to OPI No. 42951/82). As materials for the definite area-porous layer, the same materials as used for the porous spreading layer can be employed and, in addition thereto, any material can be employed so long as the interior of the material is porous and can retain a liquid such as water and the pores thereof penetrate from one major surface to the other major surface. The method for providing the definite area-porous layer onto a reagent layer, a light-reflecting layer, or the like, can be in accordance with the method disclosed in Japanese Utility Model Application No. 120299/80 or the method for providing the porous spreading layer described above.

As light-reflecting layer 40 (thickness 2–15 μm), a layer having dispersed therein one or more white pigments such as finely divided titanium dioxide powder, finely divided barium sulfate powder or the like in a hydrophilic binder polymer as disclosed in Japanese Patent Applications (OPI) Nos. 53888/74 (corresponding to U.S. Pat. No. 3,992,158), 40191/76 (corresponding to U.S. Pat. No. 4,042,335), 164356/80 (corresponding to U.S. Pat. No. 4,292,272), etc., a blush polymer layer (membrane filter) having dispersed therein one or more white pigments such as finely divided titanium dioxide powder, finely divided barium sulfate powder or the like as disclosed in Japanese Patent Application (OPI) No. 53888/74 (corresponding to U.S. Pat. No. 3,992,158), etc., a blush polymer layer as disclosed in Japanese Patent Application (OPI) No. 53888/74 (corresponding to U.S. Pat. No. 3,992,158) etc., a water-permeable layer comprising a porous metal layer as disclosed in Japanese Patent Application (OPI) No. 26428/80, a water-permeable layer containing one or more metal powders as disclosed in Japanese Patent Application (OPI) No. 26429/80, etc. can be employed; techniques for providing these layers can be in accordance with the methods as disclosed in the specifications described above.

Figure 6:
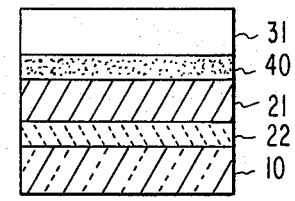

FIG. 6 shows a quantitative analysis film having a structure comprising support 10 having provided thereon, in sequence, color-forming reaction layer 22 containing the color indicator for detecting hydrogen peroxide, dye-fixing layer 21 containing the mordanting polymer, light-reflecting layer 40 and porous spreading layer 31 and has a structure such that the positional relationship of the color-forming reaction layer to the dye-fixing layer is reversed in the quantitative analysis film shown in FIG. 5. The positional relationship of the color-forming reaction layer to the dye-fixing layer can be freely chosen except that a cationic compound that absorbs light at the wavelength region (generally about 400 to about 700 nm) at which the cationic dye formed by the color indicator for detecting hydrogen peroxide absorbs should not be used as such interferes with colorimetric analysis. Accordingly, this positional relationship is effective in the case where it is desired to provide the color-forming reaction layer as a lower layer so that it will not contact the air, e.g, where a component in the color indicator for detecting hydrogen peroxide might be oxidized by air, etc.

Figure 7:
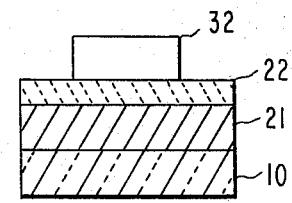

FIG. 7 indicates a quantitative analysis film having a structure comprising support 10 having provided thereon, in sequence, dye-fixing layer 21 containing the mordanting polymer, color-forming reaction layer 22 containing the color indicator for detecting hydrogen peroxide and further thereon a porous layer which is porous and has a definite area which is determined so that a liquid sample can be supplied thereto in an amount greater than that of water which can be held in the porous layer and transferred into color forming reaction layer 22 in the thus determined amount of the liquid sample with the same width as that of layer 32, i.e., definite area-porous layer 32 in close contact. A quantitative analysis film having a definite area-porous layer is suited for analysis of the hydrogen peroxide content in an aqueous liquid sample particularly containing a small quantity of hydrogen peroxide. A light-reflecting layer can be provided between a color-forming reaction layer and a definite area-porous layer. Further, the location of a color-forming reaction layer and a dye-fixing layer can also be reversed (as in the case of the quantitative analysis film as shown in FIG. 6).

Figure 8:
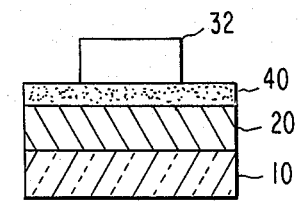

FIG. 8 indicates a quantitative analysis film having a structure comprising support 10 having provided thereon, in sequence, reagent layer 20 containing the color indicator for detecting hydrogen peroxide and the mordanting polymer, light-reflecting layer 40 and definite area-porous layer 32. In FIG. 7 and FIG. 8, the definite area-porous layer is illustrated to have a size smaller than those of the other layers; however, it is sufficient if the definite area-porous layer is designed to have a shape and size of not greater than those of the color-forming reaction layer or the reagent layer and, accordingly, the definite area-porous layer may have the same shape and size as the color-forming reaction layer or the reagent layer, as shown in FIG. 8.

As supports for the quantitative analysis films as shown in FIGS. 3 through 8, films or sheets of a variety of polymers such as polyethylene terephthalate, cellulose esters (cellulose diacetate, cellulose triacetate, cellulose acetate propionate, etc.), polycarbonates (polycarbonate of bisphenol A, etc.), polymethyl methacrylate, polystyrene, etc., having a thickness of about 25 μm to about 0.3 mm, preferably about 50 μm to about 0.2 mm, can be employed.

Supports which are colorless transparent or transparent to light having wavelengths which the cationic dye formed from the color indicator for detecting hydrogen peroxide absorbs can be employed. In addition, supports which are rendered light-blocking by incorporating pigments therein (e.g., finely divided titanium oxide powder, finely divided barium sulfate powder, finely divided zinc oxide powder, carbon black), etc., can also be employed. In the case that light-blocking supports are employed, colorimetric measurement can be performed after stripping off and removing the support upon colorimetric measurement by measuring reflection light from the side free of the support. The use of a light-blocking support is advantageous in the case where reagent components liable to be photodecomposed are incorporated into a reagent layer, a color-forming reaction layer or a dye-fixing layer.

The reagent layer, the color-forming reaction layer or the dye-fixing layer of the quantitative analysis film in accordance with the present invention can contain an analyte component which differs from hydrogen peroxide (hereafter referred to as an "analyte precursor component") and a reagent composition system capable of forming hydrogen peroxide through chemical reaction (hereafter referred to as a "reagent system for forming hydrogen peroxide"). Alternatively, a reagent layer containing the reagent system for forming hydrogen peroxide (hereafter referred to as an "hydrogen peroxide-forming reagent layer") can also be provided separately from the reagent layer, the color-forming reaction layer or the dye-fixing layer. The hydrogen peroxide forming reagent layer can be any reagent composition system in which hydrogen peroxide is produced from the analyte precursor component through chemical reaction in one step or a reagent composition system in which hydrogen peroxide is produced from the analyte precursor component through chemical reactions comprising continuous enzyme reactions (e.g., cholesterol ester $\xrightarrow{\text{cholesterol esterase}}$ cholesterol $\xrightarrow{\text{cholesterol oxidase}}$ H$_2$O$_2$)

in a plurality of steps. Depending upon the hydrogen peroxide-forming reagent system, the reagent system for forming hydrogen peroxide can be incorporated into the reagent layer, the color-forming reaction layer or the dye-fixing layer, or a single layer or a plurality of layers different from the aforesaid layer can be provided as the hydrogen peroxide-forming reagent layer. Such is well known to one skilled in the art.

Examples of analyte precursor components and reagent systems for forming hydrogen peroxide include a system comprising cholesterol esters and cholesterol (as analyte precursors; hereafter the same)-cholesterol esterase and cholesterol oxidase (as the reagent system for forming hydrogen peroxide; hereafter the same) as disclosed in Japanese Patent Applications (OPI) Nos. 137192/75 (corresponding to U.S Pat. No. 3,983,005), 131588/75 (corresponding to U.S. Pat. No. 3,869,349), 124499/80 (corresponding to U.S. Pat. No. 4,269,938), etc.; a system comprising glucose-glucose oxidase as disclosed in Japanese Patent Applications (OPI) Nos. 53888/74 (corresponding to U.S. Pat. No. 3,992,158), 40191/76 (corresponding to U.S. Pat. No. 4,042,335), 124499/80 (corresponding to U.S. Pat. No. 4,269,938), 164356/80, etc.; a system comprising triglycerides-glycerine, lipase, glycerine kinase, α-glycerophosphate oxidase, etc. as disclosed in Japanese Patent Applications (OPI) Nos. 24892/78 (corresponding to U.S. Pat. No. 4,241,178), 24893/78, 26382/78 (corresponding to U.S. Pat. No. 4,179,334), etc.; a system comprising lactic acid salts and lactic acid-lactate dehydrogenase and lactate oxidase as disclosed in Japanese Patent Applications (OPI) Nos. 105292/78, 73096/79 (corresponding to U.S. Pat. No. 4,184,923), etc.; a system comprising urikase and a hydrogen peroxide-forming reagent capable of reacting with or containing any one of the foregoing substances as disclosed in U.S. Pat. No. 4,062,731, Japanese Patent Applications (OPI) Nos. 50393/79 (corresponding to U.S. Pat. No. 4,283,491), 124499/80 (corresponding to U.S. Pat. No. 4,269,938), etc. Needless to say, the analyte precursor components and the hydrogen peroxide-forming reagent systems are not limited to those as described above and other hydrogen peroxide-forming reagent systems for analyte precursor components can also be employed.

In the case that the quantitative analysis film of the present invention—including the embodiments shown in FIGS. 2 through 8—takes a multi-layered composite structure, methods as disclosed in Japanese Patent Applications (OPI) Nos. 53888/74 (corresponding to U.S. Pat. No. 3,992,158), 40191/76 (corresponding to U.S. Pat. No. 4,042,335), 90859/80 (corresponding to U.S. Pat. No. 4,258,001) and 164356/80, Japanese Patent Application No. 140532/80, Japanese Patent Applications (OPI) Nos. 26428/80 and 26429/80, Japanese Utility Model Application No. 120299/80, etc., described above can be used to form the same; alternatively, the quantitative analysis film can be prepared using known various coating techniques established as methods for preparing conventional color photographic light sensitive materials, instant black-and-white or color photographic light sensitive materials as they are or by slightly modifying the same.

A method for quantitatively assaying hydrogen peroxide using the quantitative analysis film of the present invention will be explained below. Procedures for quantitative analysis using the quantitative analysis film of the present invention include dropping a liquid sample to be tested onto the quantitative analysis film, measurement of the optical density of a color formed on the dye-fixing layer and incubation after spotting, depending upon necessity. Dropping and incubation of a liquid sample to be tested can be performed under conventional conditions (generally at temperatures of from about 15° to about 40° C. for 2 to 20 mins. using equipment for dropping a sample liquid and measurement devices in accordance with the method disclosed in the aforesaid patent specifications or Japanese Patent Applications (OPI) Nos. 81292/78 (corresponding to U.S. Pat. No. 4,224,032), 76044/78 (corresponding to U.S. Pat. No. 4,119,381) and 76095/78 (corresponding to U.S. Pat. No. 4,152,390), Japanese Patent Application No. 154313/79, Japanese Utility Model Applications Nos. 45527/80 and 103204/80, etc. In the case the quantitative analysis films have structures as shown in FIGS. 4 to 8, quantitative analysis can be performed with extremely high accuracy by dropping a trace amount of a sample liquid within the range of from 5 μl to 50 μl. On the other hand, in the case that the quantitative analysis films as shown in FIGS. 1 through 3 are employed, quantitative analysis can be performed by immersing the quantitative analysis films in a sample liquid to be tested, leaving them, if necessary, incubating the same and then subjecting them to colorimetric measurement. In this case, analysis can be performed using devices for colorimetric measurement as disclosed in Japanese Patent Applications (OPI) Nos. 82685/76 and 144293/76, Japanese Utility Model Application (OPI) No. 134381/77, etc.

Having thus generally described the invention, the following Examples are given to further illustrate the same.

EXAMPLE 1

A solution for a dye-fixing layer having the following composition was coated onto a colorless transparent polyethylene terephthalate (PET) film having a thickness of 180 μm for photographic use in a dry thickness of 5 μm followed by drying to thereby provide the dye-fixing layer.

| Composition of Solution for Dye-Fixing Layer: | |
|---|---|
| Potassium polystyrene-p-sulfonate | 5 g. |
| Gelatin | 10 g. |
| Surfactant 10G ® | 1 g. |
| (50 wt % aqueous solution of n-C$_9$H$_{19}$—C$_6$H$_4$—(CH$_2$CH(OH)—CH$_2$—O—)$_{10}$H) | |
| Water | 100 ml. |

Then, a coating solution having the following composition for a reagent layer was coated on the dye-fixing layer in a dry thickness of 10 μm and dried to provide a reagent layer.

| Composition of Solution for Reagent Layer: | |
| --- | --- |
| N,N—Bis(β-hydroxyethyl)-m-toluidine | 100 mg. |
| 4-Aminoanitpyrine hydrochloride | 120 mg. |
| Propyl gallate | 50 mg. |
| Gelatin | 3.2 g. |
| Surfactant 10G ® | 100 mg. |
| Peroxidase | 1100 units |
| Water | 15 ml. |

Onto the thus prepared multilayer film, a membrane filter (Fuji Microfilter-500 ®, made by Fuji Photo Film Co., Ltd.) composed of cellulose triacetate containing finely divided titanium dioxide was laminated by means of wet pressing to give a multilayer analysis film (El) for detecting hydrogen peroxide of the present invention.

The thus obtained film was cut into a size having an area of 0.5 cm². Onto the uppermost membrane filter, 8 μl each of aqueous solutions of hydrogen peroxide having a variety of concentrations prepared in a standard manner was dropped and incubation at 30° C. for 5 mins. followed. An optical density of each of the formed colors was measured as a reflection optical density. Results obtained are shown in the table below.

TABLE 1

| Concentration of Hydrogen Peroxide in Aqueous Hydrogen Peroxide Solution | Reflection Optical Density (measured through a green filter) |
| --- | --- |
| 0 (blank test) | 0.17 |
| $10^{-3}$ mol/l | 1.50 |
| $5 \times 10^{-3}$ mol/l | 2.20 |
| $10^{-2}$ mol/l | 2.80 |

Comparison Example 1

A multilayer analysis film (Cl) for detecting hydrogen peroxide was prepared as in Example 1 except that a coating solution for a reagent layer having the same composition as that of Example 1 except for containing no propyl gallate was employed.

Using an aqueous solution of hydrogen peroxide, a color was formed on quantitative analysis films (El) and (Cl) in a similar manner. Optical densities of the formed colors were almost the same. In more detail, reflection optical density of each of the analysis films was 2.80 (El) and 2.83 (Cl), respectively, when measured through a green filter using 8 μl of an aqueous solution of $10^{-2}$ mol/l hydrogen peroxide.

Then, quantitative analysis films (El) and (Cl) were subjected to a forced deterioration test with the passage of time under the following conditions:

(a) drying condition at 45° C. (which means that the analysis film was stored in a sealed container in which a sufficient amount of a drying agent (silica gel powders) was present; hereafter the same); and, (b) 25° C., 50% RH (humidity).

After a definite period of time passed, each of the analysis films was permitted to form a color by dropping a $10^{-2}$ mol/l aqueous hydrogen peroxide solution thereon as described above to form a color. The reflection optical density observed (through a green filter) after the forced deterioration test is expressed by the proportion thereof to a fresh reflection optical density prior to the forced deterioration test, which is shown in Tables 1 and 2.

TABLE 1

Color Density and Color Formation Rate of Analysis Film After Forced Test Under Drying at 45° C.

| Analysis Film | Fresh | 1 Day | 2 Days | 10 Days | 20 Days |
| --- | --- | --- | --- | --- | --- |
| (E1) | 2.80 | 100% | 99% | 95% | 95% |
| (C1) | 2.83 | 100% | 63% | 34% | 30% |

TABLE 2

Color Density and Color Formation Rate of Analysis Film After Forced Test at 25° C., 50% RH

| Analysis Film | Fresh | 10 Days | 30 Days | 60 Days |
| --- | --- | --- | --- | --- |
| (E1) | 2.80 | 100% | 99% | 97% |
| (C1) | 2.80 | 22% | 13% | 10% |

As is seen from the results in the tables, the analysis films of the present invention showed excellent color formation even after the deterioration test.

EXAMPLE 2

A quantitative analysis film for detecting hydrogen peroxide was prepared as in Example 1 except that various antioxidants as shown in Table 3 were incorporated, instead of propyl gallate. With the thus prepared analysis films, a forced thermal test was performed under a drying condition at 45° C. Evaluation was made as in Example 1. Results obtained are shown in Table 3, in which symbols for evaluation indicate:

TABLE 3

Effect of Various Antioxidants on Preventing Deterioration Due To POD

| | Reduction Rate of Reflection Optical Density (%) | | | |
| --- | --- | --- | --- | --- |
| Antioxidant | 1 Day | 6 Days | 10 Days | Judgement |
| 2,6-Di-t-butyl-4-methylphenol | 66 | 90 | 92 | x |
| 2,5-Dihexyl-hydroquinone | 64 | 84 | 86 | x |
| Bisphenol A | 72 | 88 | 91 | x |
| Methyl gallate | 0 | 2 | 3 | o |
| Isoamyl gallate | 0 | 15 | 25 | o |
| 5-Ethylpyrogallol | 0 | 15 | 25 | o ~ Δ |
| 1,7-Dihydroxy-naphthalene | 0 | 11 | 52 | x (additionally formed reddish color) |
| Isobutyl gallate | 0 | 1 | 2 | o | o: Reduction in reflection optical density is extremely small (this invention).
Δ: Reduction in reflection optical density is small (this invention).
x: Reduction in reflection optical density is serious (impossible to put in practical use) (comparison).

From the results above, it is understood that the pyrogallol derivatives effectively prevented deterioration due to POD.

EXAMPLE 3

A multilayer analysis film for glucose analysis was prepared as in Example 1 except that isobutyl gallate was employed in place of propyl gallate in the composition of a coating solution for the reagent layer of Example 1 and 1500 units of glucose oxidase were further incorporated therein.

This analysis film was cut into a square of 1.5×1.5 cm. Onto the membrane filter layer (porous spreading layer) of this analysis film, 10 μl of control serum commercially available, which was adjusted the glucose content to 100, 200, 300 and 500 mg/dl, respectively, by adding glucose to the serum, was dropped and incubation at 37° C. for 5 mins. followed to form a color.

In case where 50 mg. of isobutyl gallate was used, results as shown in Table 4 below were obtained.

TABLE 4

| Aqueous Solution of Glucose | Reflection Optical Density (measured at a wavelength of 600 nm) |
|---|---|
| 100 | 0.73 |
| 200 | 1.14 |
| 300 | 1.48 |
| 500 | 1.97 |

This analysis film was subjected to a forced deterioration test with the passage of time under the drying condition at 45° C. The same color formation test was performed 20 days after. The reduction rate of reflection optical densities was 0% in a range of from 100 mg/dl to 500 mg/dl in the glucose content in an aqueous solution. That is, reflection optical densities were not reduced at all even 20 days after.

In a similar manner, the forced deterioration test with the passage of time under the drying condition at 45° C. was performed using other gallic acid esters. The same color formation test was likewise performed 20 days after. The reduction rate in reflection optical densities in average is indicated by percentage in Table 5 below, in a range of from 100 mg/dl to 500 mg/dl in the glucose content.

TABLE 5

| Gallic Acid Ester | Reduction Rate in Reflection Optical Density (%) |
|---|---|
| Isobutyl gallate | 0 |
| Propyl gallate | 0 |
| Butyl gallate | 1 |
| Isoamyl gallate | 1 |
| Methyl gallate | 3 |
| Octyl gallate | 5 |

EXAMPLE 4

| Composition of Coating Solution for Dye-Fixing Layer: | |
|---|---|
| Aqueous latex solution (30%) of poly(N,N,N—trimethyl-N—(vinylbenzyl) ammonium chloride | 15 g. |
| Gelatin | 10 g. |
| Surfactant 10G ® | 1 g. |
| Water | 80 g. |
| Composition of Coating Solution for Reagent Layer: | |
| 1,7-Dihydroxynaphthalene | 80 mg. |
| 4-Aminoantipyrine hydrochloride | 120 mg. |
| Ethyl gallate | 20 mg. |
| Gelatin | 3.2 g. |
| Surfactant 10G ® | 100 mg. |
| Peroxidase | 1100 units |
| Water | 15 ml. |

Onto a colorless transparent PET film having a dry thickness of 180 μm, the coating solution for a dye-fixing layer and the coating solution for a reagent layer described above were coated, in sequence, as in Example 1 (dry thickness of the dye-fixing layer, 5 μm; dry thickness of the reagent layer, 10 μm).

Then, a coating solution having the following composition for a light blocking layer (light shielding or reflecting layer) was coated on the reagent layer in a dry thickness of 7 μm, followed by drying.

| Composition of Coating Solution for Light Blocking Layer: | |
|---|---|
| Finely divided TiO$_2$ powder | 19.5 g. |
| Gelatin | 6.8 g. |
| Sodium dioctylsulfosuccinate | 1.0 g. |
| Water | 87 g. |

Cotton broadcloth having 100 counts and a thickness of 180 μm was further wet-pressed on the thus prepared coating laminate to prepare a multilayer analysis film (E4) for detecting hydrogen peroxide.

COMPARISON EXAMPLE 2

A multilayer analysis film (C2) for detecting hydrogen peroxide was prepared as in Example 4 except that a coating solution for a reagent layer having the same composition as that for the reagent layer of Example 4 except for containing no ethyl gallate therein was employed.

After subjecting the analysis films (E4) and (C2) to a forced deterioration test for 2 weeks under the drying condition at 45° C., aqueous solutions of hydrogen peroxide were dropped on the analysis films, respectively, and, incubation at 30° C. for 5 mins. followed. Thereafter, a reflection optical density of each of the formed colors was measured. The reduction rate of the reflection optical density in average was as follows.

Analysis film (E4): 2%
Analysis film (C2): 50%

While the invention has been described in detail and with reference to specific embodiments thereof, it will be apparent to one skilled in the art that various changes and modifications can be made therein without departing from the spirit and scope thereof.

What is claimed is:

1. In a color indicator composition for detecting hydrogen peroxide comprising a substance having peroxidase activity and a substance capable of causing a detectable change in the presence of hydrogen peroxide and said substance having a peroxidase activity, the color indicator composition for detecting hydrogen peroxide comprising a pyrogallol derivative represented by formula (1):

$$\text{(1)}$$

[Structure: benzene ring with OH at top, HO and OH at meta positions, and Q$^1$ at bottom]

wherein Q$^1$ represents a nitro group, a cyano group, an alkyl group, a substituted alkyl group, an aryl group, a substituted aryl group, an aralkyl group, a carboxyl group or a —COOQ$^2$ group wherein Q$^2$ represents an alkyl group, a substituted alkyl group, an aryl group, a substituted aryl group or an aralkyl group.

2. The color indicator composition for detecting hydrogen peroxide of claim 1 wherein said substance capable of causing a detectable change is a combination of a hydrogen donor and a coupler.

3. The composition of claim 2 wherein said hydrogen donor is at least one compound selected from the group consisting of a 4-substituted antipyrine, a 2-hydrazinobenzothiazoline, a p-halogenophenol and an N,N-disubstituted-p-phenylenediamine represented by formula (2):

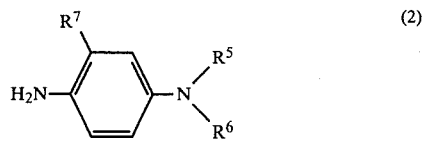

wherein $R^5$ and $R^6$ each represents an alkyl group, an alkoxyalkyl group, a hydroxyalkyl group, a cyanoalkyl group, a halogenoalkyl group or an acylaminoalkyl group and, $R^5$ and $R^6$ may be the same or different; and $R^7$ represents a hydrogen atom, an alkyl group, an akoxy group or a halogen atom.

4. The composition of claim 2 wherein said coupler is at least one compound selected from the group consisting of a naphthol, a phenol, a pyrazolone and an N,N-disubstituted aniline represented by formula (3):

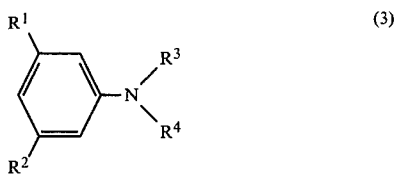

wherein $R^1$ and $R^2$ each represents a hydrogen atom, an alkyl group or an alkoxy group and, $R^1$ and $R^2$ may be the same or different; and $R^3$ and $R^4$ each represents an alkyl group, an alkoxyalkyl group, a hydroxyalkyl group, an aminoalkyl group, a cyanoalkyl group, a halogenoalkyl group or an acylaminoalkyl group and, $R^3$ and $R^4$ may be the same or different.

5. The composition of claim 3 wherein said hydrogen donor is 4-aminoantipyrine.

6. In a quantitative analysis film which comprises a support and a reagent layer having contained therein a color indicator composition for detecting hydrogen peroxide comprising a substance having a peroxidase activity and a substance capable of causing a detectable change in the presence of hydrogen peroxide and the substance having a peroxidase activity, the quantitative analysis film wherein the composition contains a pyrogallol derivative represented by formula (1):

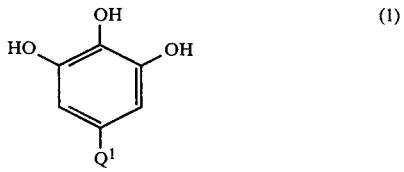

wherein $Q^1$ represents a nitro group, a cyano group, an alkyl group, a substituted alkyl group, an aryl group, a substituted aryl group, an aralkyl group, a carboxyl group or a —$COOQ^2$ group wherein $Q^2$ represents an alkyl group, a substituted alkyl group, an aryl group, a substituted aryl group or an aralkyl group.

7. The quantitative analysis film of claim 6 wherein said substance capable of causing a detectable change is a combination of a hydrogen donor and a coupler.

8. The quantitative analysis film of claim 6 wherein said reagent layer is further composed of a color-forming reaction layer and a dye-fixing layer.

9. The quantitative analysis film of claim 6 wherein said reagent layer is a single layer.

10. The quantitative analysis film of claim 7, wherein said hydrogen donor is at least one compound selected from the group consisting of a 4-aminoantipyrine, a 2-hydrazinobenzothiazoline, a p-halogenophenol and an N,N-disubstituted-p-phenylenediamine represented by formula (2):

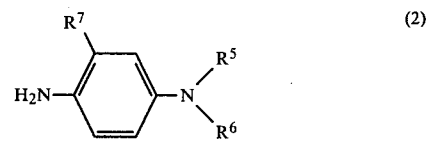

wherein $R^5$ and $R^6$ each represents an alkyl group, an alkoxyalkyl group, a hydroxyalkyl group, a cyanoalkyl group, a halogenoalkyl group or an acylaminoalkyl group and, $R^5$ and $R^6$ may be the same or different; and $R^7$ represents a hydrogen atom, an alkyl group, an alkoxy group or a halogen atom.

11. The quantitative analysis film of claim 7, 8 or 9 wherein said coupler is at least one compound selected from the group consisting of a naphthol, a phenol, a pyrazolone and an N,N-disubstituted aniline represented by formula (3):

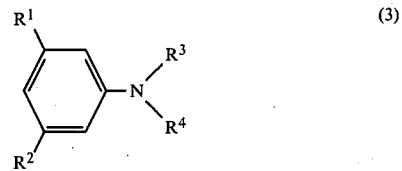

wherein $R^1$ and $R^2$ each represents a hydrogen atom, an alkyl group or an alkoxy group and, $R^1$ and $R^2$ may be the same or different; and $R^3$ and $R^4$ each represents an alkyl group, an alkoxyalkyl group, a hydroxyalkyl group, an aminoalkyl group, a cyanoalkyl group, a halogenoalkyl group or an acylaminoalkyl group and, $R^3$ and $R^4$ may be the same or different.

12. The quantitative analysis film of claim 7, wherein said hydrogen donor is 4-aminoantipyrine.

13. The quantitative analysis film of claim 7, wherein said reagent layer is provided between a support and a porous layer and, the porous layer is in a fluid contact with the reagent layer to form an integral form.

14. The quantitative analysis film of claim 7, wherein said composition is contained in a polymer binder.

15. The quantitative analysis film of claim 7, wherein said reagent layer further contains a mordanting agent comprising an anionic polymer or a cationic polymer.

16. The quantitative analysis film of claim 8 wherein said dye-fixing layer further contains a polymer mordanting agent comprising an anionic polymer or a cationic polymer.

17. The quantitative analysis film of claim 6 wherein said support is porous and impregnated with said composition.

* * * * *